US012527661B2

(12) United States Patent
Lee et al.

(10) Patent No.: US 12,527,661 B2
(45) Date of Patent: Jan. 20, 2026

(54) INTRAOCULAR LENS CLIP AND METHOD OF FIXING INTRAOCULAR LENS

(71) Applicant: Vincent Yau Wing Lee, Central (HK)

(72) Inventors: Audrey Lee, Pokfulam (HK); Annabelle Lee, Pokfulam (HK); Vincent Yau Wing Lee, Pokfulam (HK); Dennis Shun Chiu Lam, Central (HK)

(73) Assignee: Vincent Yau Wing Lee, Pokfulam (HK)

( * ) Notice: Subject to any disclaimer, the term of this patent is extended or adjusted under 35 U.S.C. 154(b) by 305 days.

(21) Appl. No.: 18/185,693

(22) Filed: Mar. 17, 2023

(65) Prior Publication Data

US 2024/0307171 A1 Sep. 19, 2024

(51) Int. Cl.
*A61F 2/16* (2006.01)

(52) U.S. Cl.
CPC .................................. *A61F 2/1664* (2013.01)

(58) Field of Classification Search
CPC ......... A61F 2/1662; A61F 2/16; A61F 2/1664
See application file for complete search history.

(56) References Cited

U.S. PATENT DOCUMENTS

2007/0052923 A1* 3/2007 Ayyagari .............. A61F 2/1664 351/159.73
2022/0079744 A1 3/2022 Arrieta

OTHER PUBLICATIONS

"Aneurysm Clipping," UC Neuroscience Institute, 2020, 4 pages.
Tzu et al., "Use of a microvascular clip for iris fixation of an intraocular lens," Surgical Technique, American Medical Association, 2010, 3 pages.

* cited by examiner

*Primary Examiner* — Vi X Nguyen
(74) *Attorney, Agent, or Firm* — ROTHWELL, FIGG, ERNST & MANBECK, P.C.

(57) ABSTRACT

This application discloses an intraocular lens (IOL) clip for fixing an IOL to the sclera of an eye. The IOL clip includes a first arm, a second arm opposing the first arm and a portion joining the first arm and the second arm. The IOL clip has an open state in which an IOL haptic can be introduced into a gap between the first arm and the second arm and a closed state for gripping the IOL haptic between the first arm and the second arm. The IOL clip includes a scleral fixator for attaching the IOL clip to the sclera. The scleral fixator includes a shaft and a flange.

9 Claims, 11 Drawing Sheets

12
14
16

12
14
16

12
14

12
14

12
14

12
14

INTRAOCULAR LENS CLIP AND METHOD OF FIXING INTRAOCULAR LENS

TECHNICAL FIELD

The present disclosure relates to a clip for fixing an intraocular lens (IOL) to the sclera of an eye and a method of fixing an intraocular lens to the sclera of the eye.

BACKGROUND

The crystalline lens, together with the cornea form the main refractive elements of the human eye which focus incident light onto the retina. When a cataract forms, the crystalline lens becomes cloudy or opaque and vision is blurred. Normal vision may be restored through cataract surgery. In cataract surgery, the nucleus and cortex which form the bulk of the crystalline lens are removed, leaving behind an intact lens capsule, which is a thin membrane around the natural lens. The lens capsule is sometimes referred to as the capsular bag. An artificial intraocular lens (IOL) is then implanted into the lens capsule to restore the normal refractive power of the eye.

In a normal anatomy, the lens capsule is suspended in position by the zonule, which is an elaborate system of fibres. In some conditions, one or both of the lens capsule and the zonule are damaged, which means that the intraocular lens (IOL) cannot be implanted. These conditions may include trauma, damage from a previous cataract operation, ocular diseases such as simple ectopia lentis, pseudoexfoliation syndrome, pathological myopia and Axenfeld Rieger Syndrome, or systemic conditions such as Marfan's syndrome, Ehlers-Danlos syndrome and Eczema.

If the crystalline lens is removed and an IOL cannot be implanted, the eye is without a lens. This condition is called aphakia. Aphakic patients need to wear thick and heavy hypermetropic glasses, which restore eyesight to some extent, but provide sub-optimal vision.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

BRIEF DESCRIPTION OF DRAWINGS

Examples of the present disclosure will now be described, by way of non-limiting example only, with reference to the accompanying drawings, in which.

DESCRIPTION OF EMBODIMENTS

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps. The terms "includes" means includes but not limited to, the term "including" means including but not limited to. The term "based on" means based at least in part on. The term "number" means any natural number equal to or greater than one. The terms "a" and "an" are intended to denote at least one of a particular element.

Figure 1A:
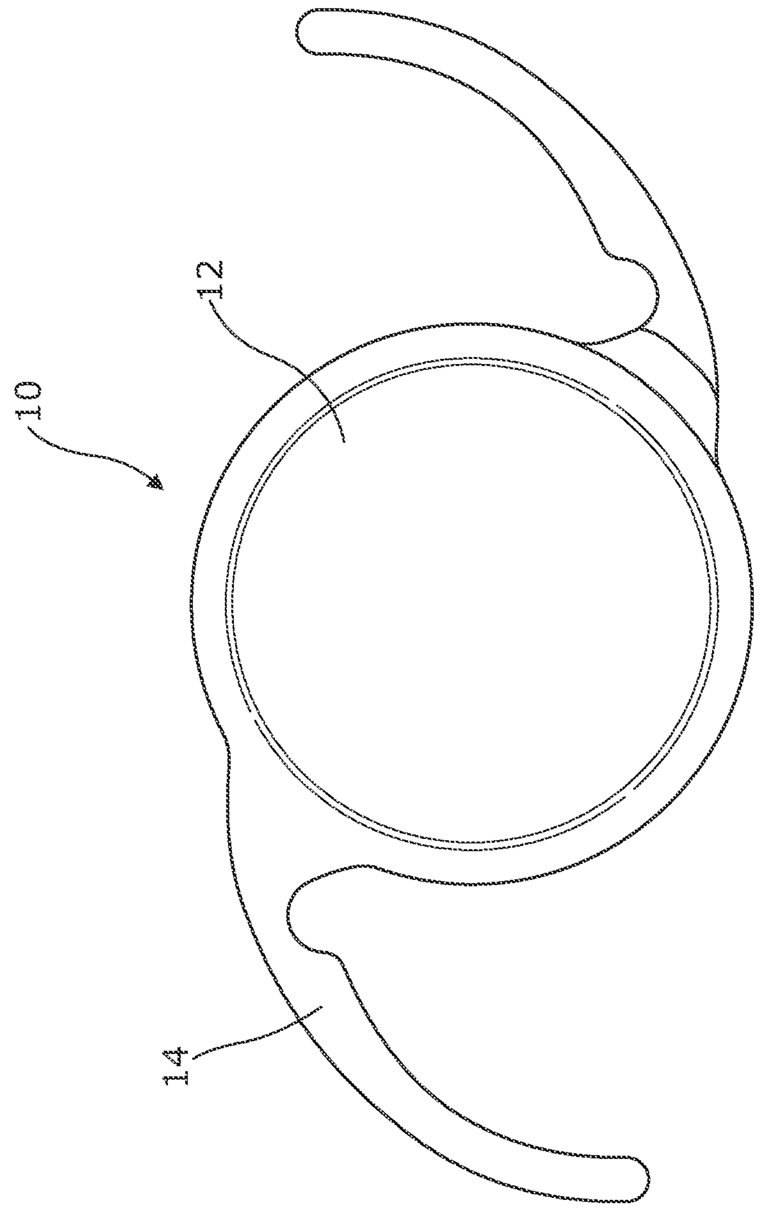
FIGS. 1A to 1L show examples of intraocular lenses (IOLs)
Figures 1B, 1C, 1D, 1E, 1F, 1G:
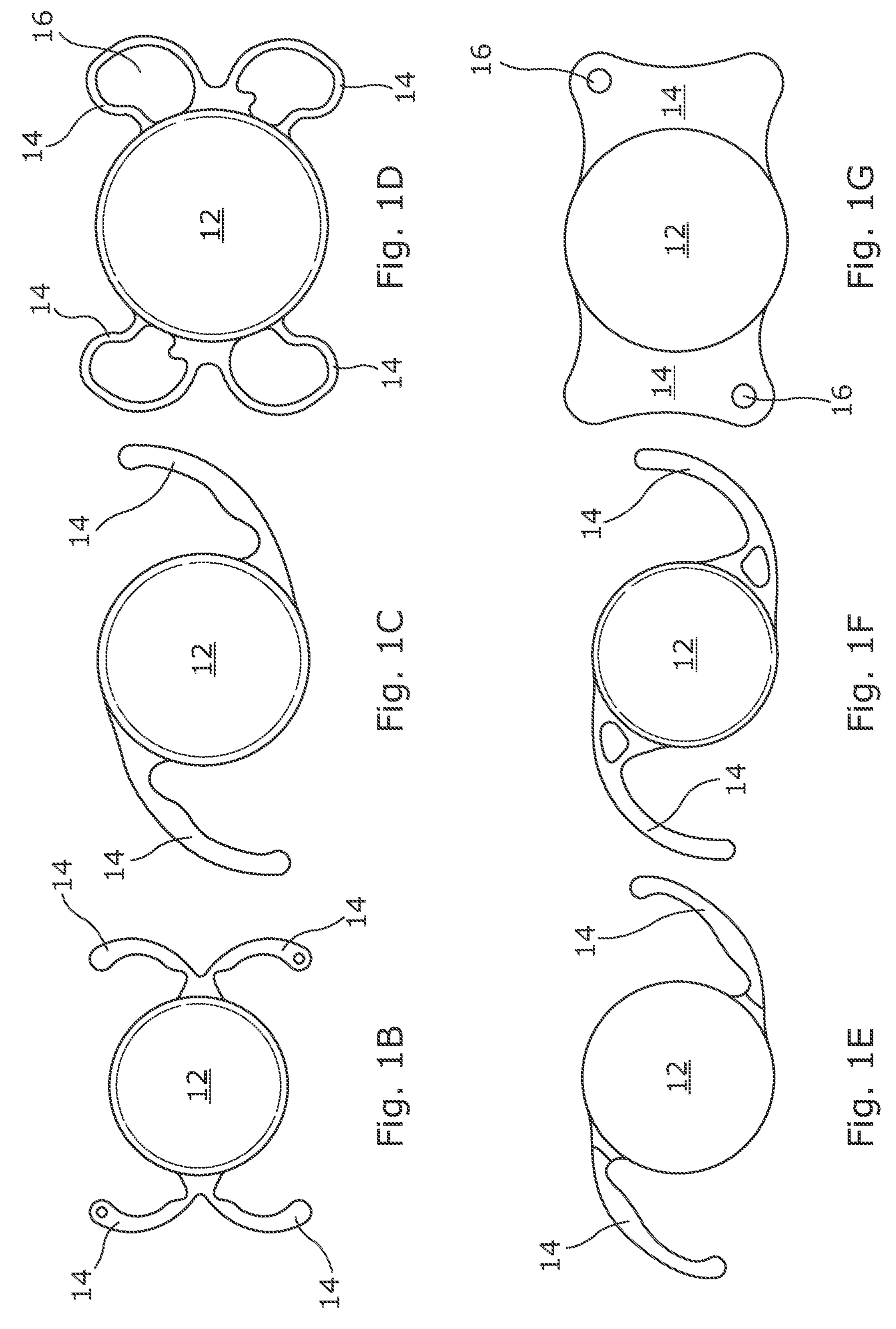

An example of an intraocular lens (IOL) 10 is shown in FIG. 1A. The IOL comprises an optic part 12 (referred to as the "optic") for refracting light and at least one haptic part 14 (referred to as the "haptic") for facilitating attachment of the IOL to the eye. The optic 12 forms a central part of the IOL, while the haptics 14 are appendages which extend outwardly from the optic.

In one-piece IOLs, the optic and haptic are formed integrally from the same piece of material. In three-piece IOLs, the optic and the haptic(s) are formed from different types of material. For example, a three-piece IOL may comprise an optic of a first material and a pair of haptics of a second material attached to the optic. Three-piece IOLs are more versatile in that they can be placed into either the capsular bag or the ciliary sulcus. In contrast, one-piece IOLs can be placed in the capsular bag, but cannot be placed in the ciliary sulcus.

Figure 1J:
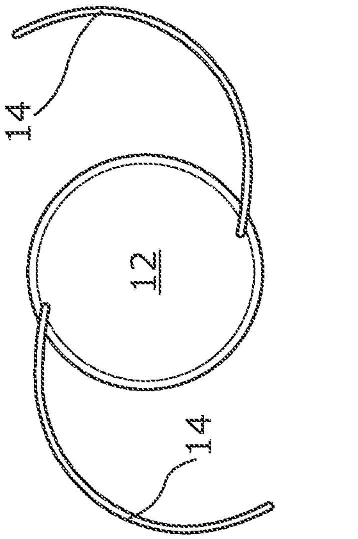
Figure 1I:
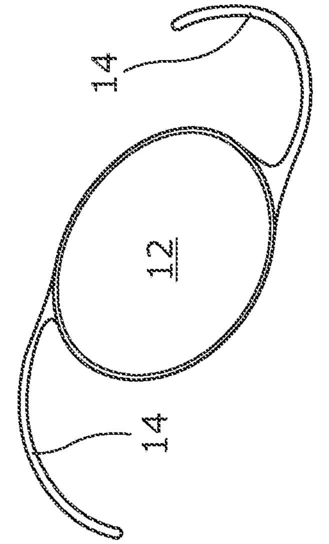
Figure 1H:
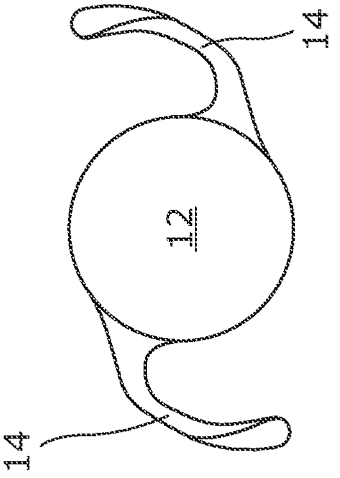
Figure 1L:
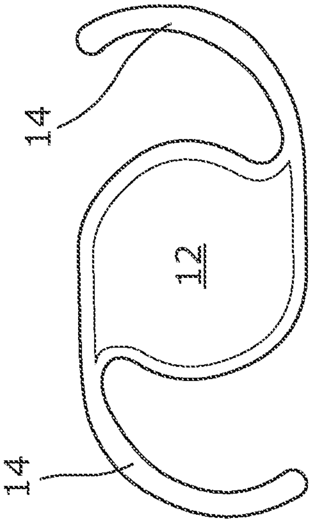
Figure 1K:
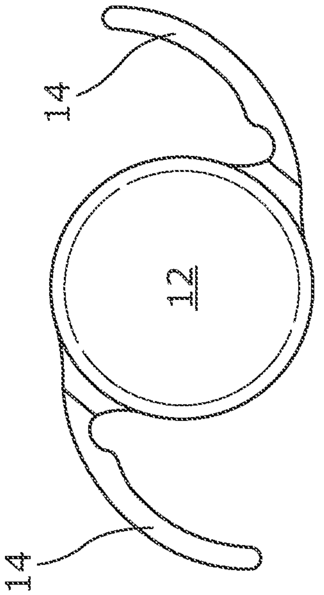

The IOL shown in FIG. 1A is a one-piece IOL with two haptics. FIGS. 1B-1L show further examples of different designs of IOL, each of which comprises an optic 12 and one or more haptics 14. FIGS. 1B-11 and 1K-1L are one-piece IOLs in which the optic and haptics are formed from the same material, while FIG. 1J is a three-piece IOL in which the optic and haptics are formed from different materials. The IOLs of FIGS. 1B and 1D have four haptics. The IOLs of FIGS. 1D and 1G have haptics 14 with one or more apertures 16 forming eyelets.

In modern cataract surgery, the IOL is ideally implanted into the capsular bag and the haptics press against the inner walls of the capsular bag to keep the IOL in place. However, this is may not be possible if the capsular bag is damaged, or if the capsular bag is unstable due to damage to the zonule which supports the capsular bag.

One approach to implanting an intraocular lens (IOL), when insufficient capsular support is available, is to suture the IOL to the sclera. In this approach, the IOL is sewn to the sclera using sterile surgical threads known as sutures. However, sutures are very fine, can break easily over time and re-suturing is a complicated task. Furthermore, suturing does not work with foldable IOLs, but only works with specially-designed rigid IOLs with eyelets. As a result, there needs to be an enlarged surgical wound through which the rigid IOL can be inserted into the eye (a wound of around 10 mm long for inserting a rigid IOL, vs a 2-3 mm surgical wound for a foldable IOL). Another approach is for the surgeon to use a needle to form a tunnel in the sclera, and place the IOL haptics into the scleral tunnel (referred to as IOL-Glue technique), but this technique only works for three-piece IOLs with tubular shape haptics (i.e. haptics which have a tube shape like a stick). Furthermore, the IOL-Glue technique is surgically demanding and has potential complications.

Another approach is to use Anterior Chamber IOLs, which are designed specifically for implantation into the anterior chamber of the eye, in the space between the cornea and the iris. This is different from the usual location for IOL implantation, which is behind the iris and inside the capsular bag. As Anterior Chamber IOLs are not implanted in the capsular bag, they do not need capsular support. However, the proximity of the Anterior Chamber IOL to the cornea, eventually leads to endothelial loss, decompensation and loss of transparency of the cornea leading to blurred vision. Anterior Chamber IOLs can also distort the pupil and cause uveitis.

The Yamane technique is another technique for fixing an IOL when there is insufficient capsular support. The Yamane technique externalises a three-piece IOL using thin walled 30-gauge needles though two transconjunctival sclerotomies. A cautery is used to make a flange at the end of the IOL haptics and this flange prevents the haptics from prolapsing back into the posterior chamber of the eye. Thus, in the Yamane technique, the IOL haptics ends are anchored to the sclera. However, the Yamanae technique only works with a very specific type of IOL, that is a three-piece IOLs having tubular shaped haptics. Furthermore, the Yamane technique is surgically demanding and has potential complications.

The present disclosure proposes a separate fixation device in the form of a clip for fixing the IOL to the sclera of an eye. As the clip is separate from the IOL, it may be used with many different types of IOL. Further, by fixing the IOL to the sclera, the IOL may be implanted and secured in the desired position even if there is insufficient capsular support. In some implementations, the clip may be used with a wide variety of different types of IOL, such as but not limited to the types of IOL shown in FIGS. 1A-1J.

A first aspect of the present disclosure provides an intraocular lens (IOL) clip for fixing an IOL to the sclera of an eye. The IOL clip may comprise a first arm, a second arm opposing the first arm and a hinge portion joining the first arm with the second arm. The hinge portion allows movement of the IOL clip between an open state, in which an IOL haptic can be introduced into a gap between the first arm and the second arm, and a closed state for gripping the IOL haptic between the first arm and the second arm. The IOL clip further comprises a scleral fixator for attaching the IOL clip to the sclera. The scleral fixator may comprise a shaft extending outwardly from the first arm, the second arm or the hinge portion and a flange on the shaft for engaging the sclera.

A second aspect of the present disclosure provides an intraocular lens (IOL) clip for fixing an IOL to the sclera of an eye. The IOL clip comprises a jaw portion comprising a pair of opposing arms for gripping a IOL haptic there between. The pair of opposing arms are movable from an open state, in which an IOL haptic may be introduced between opposing inner faces of the arms, and a closed state for gripping the IOL haptic between the inner faces of the arms. The IOL clip further comprises a scleral fixator extending from the jaw portion. The scleral fixator comprises a shaft configured to extend through the sclera and a flange configured to rest on the anterior surface of the sclera so as to hold the IOL clip in place.

A third aspect of the present disclosure provides a method of fixing an intraocular lens (IOL) to the sclera of an eye comprising: introducing the IOL into the eye; introducing a IOL clip comprising a pair of opposing arms into the eye; attaching the IOL clip to the IOL by opening the IOL clip; inserting a haptic of the IOL between the arms of the clip and closing the clip to grip the haptic; placing the IOL and the IOL clip below the plane of the iris in a posterior chamber of the eye; and attaching the IOL clip to the sclera of the eye. The IOL clip may be attached to the IOL before introducing the IOL into the eye, after introducing the IOL into the eye or while the IOL is partially inserted into the eye. In one example, the IOL clip is attached to the IOL when a leading haptic and the optic of the IOL are inside the eye and a trailing haptic is still outside the eye.

Figure 2C:
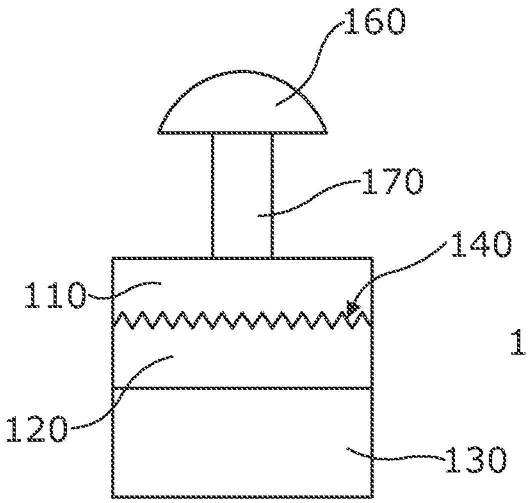
FIGS. 2A to 2D show an example of an IOL clip according to the present disclosure.
Figure 2B:
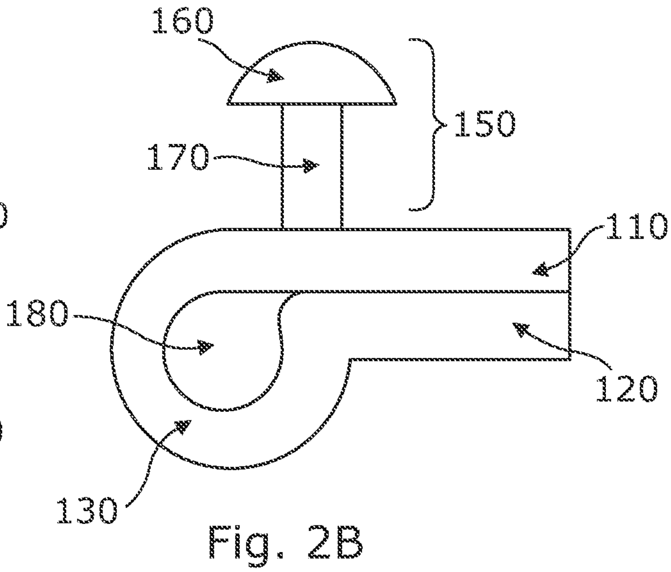
Figure 2D:
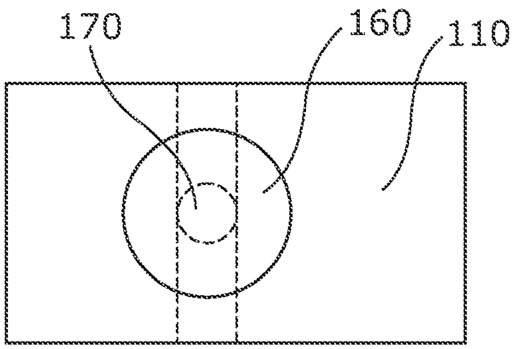
Figure 2A:
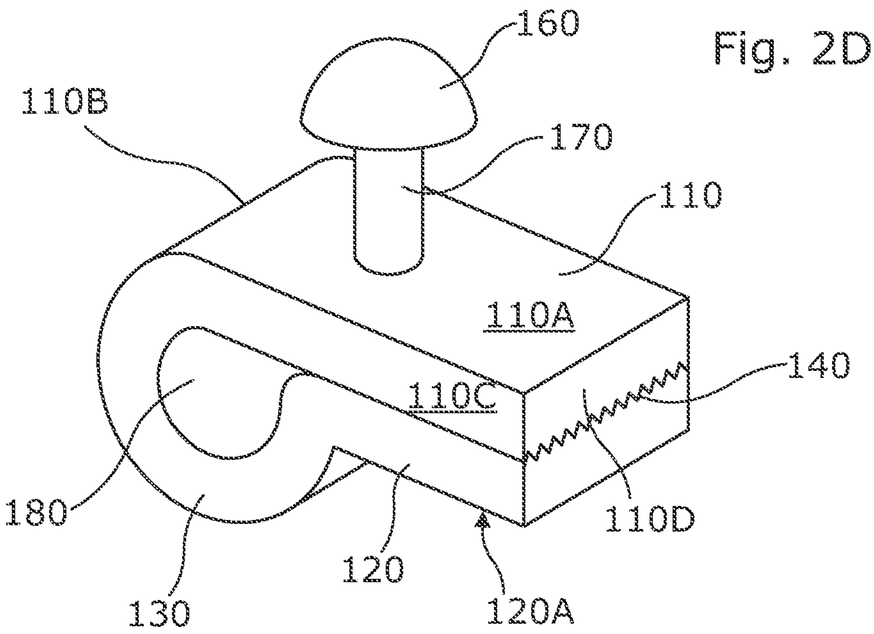

FIGS. 2A to 2D shows one example of an IOL clip 100 according to the present disclosure. FIG. 2A is a perspective view, while FIG. 2B is a view from one side, FIG. 2C is a view from one end and FIG. 2D is a view from above.

The IOL clip 100 comprises a first arm 110 and a second arm 120 opposing the first arm. The first and second arms 110, 120 together form a jaw portion for gripping an IOL haptic there between. The first arm 110 and second arm 120 may be joined by a joining portion 130, which acts as a hinge and allows the jaw to move between an open state and a closed state. In some examples the joining portion 130 may be referred to as the "hinge portion". The joining portion 130 may be considered to be part of the jaw. In FIGS. 2A-2D the IOL clip 100 is in a closed state, in which an IOL haptic may be gripped or held between the first arm 110 and the second arm 120. The IOL haptic may be gripped between an inner surface of the first arm and an inner surface of the second arm. The inner surface of the first arm and/or the inner surface of the second arm may be textured, e.g. serrated, so as to better grip the IOL haptic. In the example of FIGS. 2A-2D, the inner surfaces 140 of the first and second arms are serrated.

Figure 3:
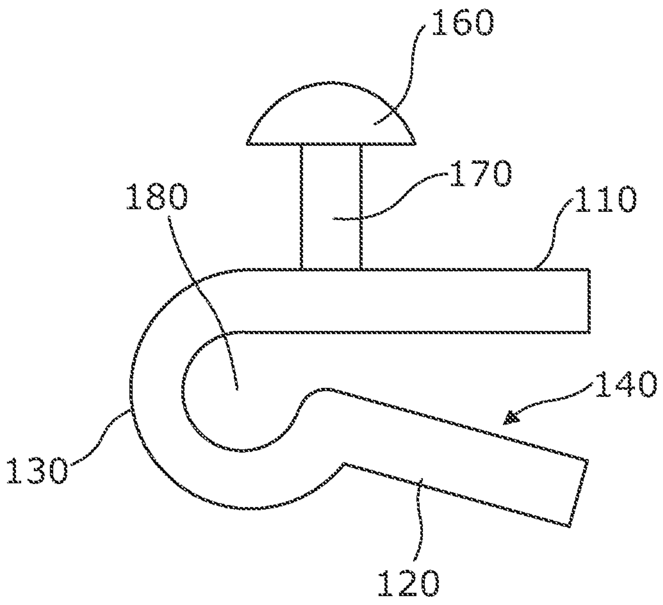
FIG. 3 shows an example of the IOL clip of FIG. 2A in an open state.

FIG. 2B is a side view of the IOL clip 100 when the IOL clip is in a closed state. FIG. 3 is a side view of the IOL clip 100 when the IOL clip is in an open state. When the IOL clip is in an open state, an IOL haptic can be introduced into a gap between the first arm 110 and the second arm 120. When the IOL clip moves back to closed state the haptic is gripped between the inner surfaces of the first and second arms.

The IOL clip 100 further comprises a scleral fixator 150 for fixing the IOL clip to the sclera of an eye. The scleral fixator 150 comprises a shaft 170 and a flange 160 on the shaft for engaging the sclera. The shaft 170 may extend outwardly from the first arm 110, the second arm 120 or the hinge portion 130. In some examples, the shaft 170 may extend outwardly from an outer face of the IOL clip. An outer face of the IOL clip refers to the upper face 110A of the first arm, the outer face 110B of the hinge portion or the lower face 120A of the second arm, rather than the edges 110C or ends 100D of the IOL clip. For example, the shaft may extend from an upper surface of the first arm or an upper surface of the hinge. In the example of FIGS. 2A-2D and FIG. 3, the shaft 170 extends from an upper surface of the first arm. In other examples, the shaft may extend from an upper surface of the hinge portion. In use, an IOL haptic is gripped between the first and second arms 110, 120 of the IOL clip, and the IOL clip is fixed to the sclera of the eye by the scleral fixator 150, so that the IOL is supported inside the eye.

The flange 160 on the shaft 170 of the scleral fixator may extend fully around the shaft, or partially around the shaft, and may have a larger diameter than shaft. In some examples, the flange 160 may take the form of a cap at the top of the shaft 170. An example of this is shown in FIGS. 2A-2D. The cap may have a smooth curved upper surface, as this helps to avoid, or minimize, damage to the conjunctiva, tenon and sclera of the eye. The cap and shaft may have a mushroom or umbrella shape, as shown in the example of FIG. 2A to 2B.

The hinge portion 130 may have inner walls which define an aperture 180. The aperture is configured for receiving a device for opening the IOL clip. In this way the IOL clip is movable from the closed state to the open state by application of pressure to inner walls of the hinge portion by the opening device. Thus the hinge or joining portion 130 defines an aperture 180 to receive a device for applying force to inner walls of the portion 130 to drive the arms 110, 120 apart from each other into an open state. The device for opening the IOL clip may, for example, be a pair of forceps or other device capable of applying pressure to the inner walls of the hinge portion. This configuration in which the hinge or joining portion 130 has an aperture 180 to receive an opening device is very convenient, as it does not take up much space and allows the same device to be used for both holding the IOL clip while it is moved to the desired position and opening the IOL clip to receive the IOL haptic.

Figure 4:
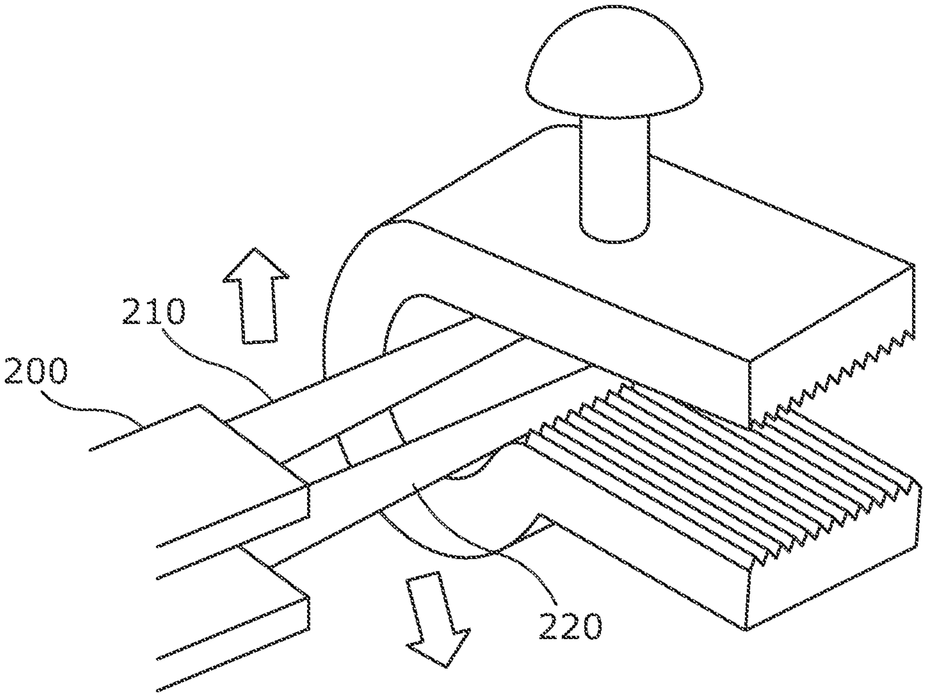
FIG. 4 shows an example of using a tool to open an IOL clip according to the present disclosure.

An example of using a device to open the IOL clip is shown in FIG. 4. The tips 210, 220 of a device 200, which in this example is a forceps device are inserted into the aperture 180. By inserting device into the aperture, the IOL clip may be held by the device and moved to the desired position within the eye. The tips 210, 220 may then be moved apart from each other, as shown by the arrows in FIG. 4, so as to apply pressure to the hinge in order to move the first arm 110 away from the second arm 120 so that the IOL clip is in an open state. In some examples the device may be a spreading forceps, such as but not limited to Watze sleeve spreading forceps.

Figure 5A:
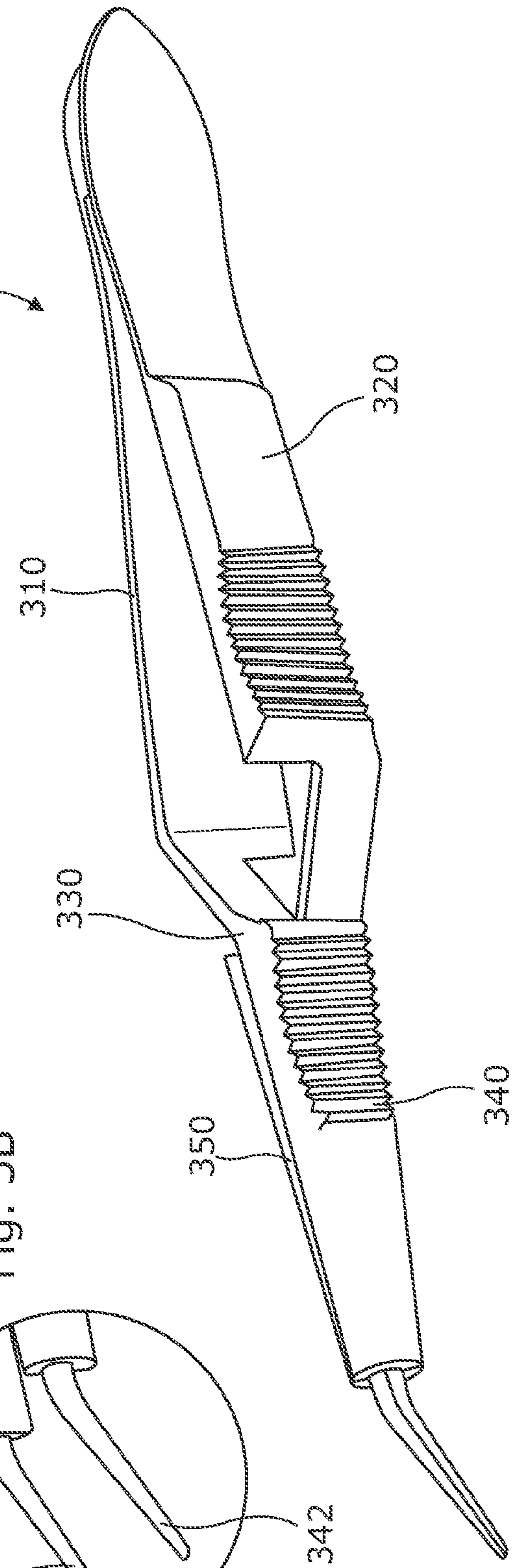
FIGS. 5A to 5B show an example of spreading forceps.
Figure 5B:
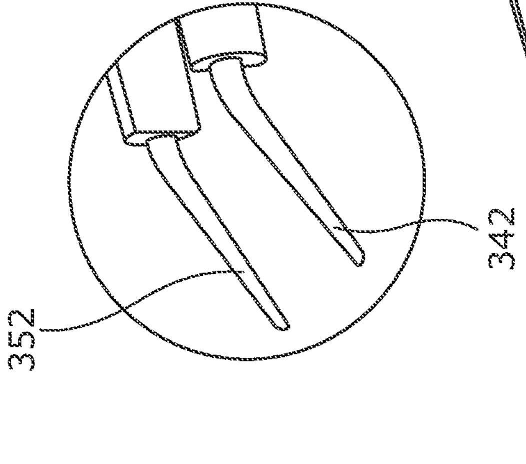

An example of spreading forceps 300 is shown in FIG. 5A. The spreading forceps 300 comprises a pair of arms which cross over each other at a crossing point 330. The portion of the arms 310, 320 on a first side of the crossing point forms a pair of handles, while the portion of the arms 340, 350 on the second side of the crossing point forms an engagement portion of the forceps ending in a pair of forceps tips 342, 352 as shown in FIG. 5B. Pressing the spreading forceps handles 310, 320 together moves the spreading forceps tips 342, 352 away from each other to the position shown in FIG. 5B. In this way the forceps tips can be moved apart to apply pressure to the inner walls of the IOL clip aperture 180 so as to open the IOL clip.

When the IOL clip is in the open state, an IOL haptic may be positioned between the arms of the IOL clip. The IOL clip may then be returned to the closed state so that the IOL haptic is held between the arms of the IOL clip. In some examples the first and second arms of the IOL clip are biased to the closed state, so that the arms return to the closed state after the force moving the IOL clip to the open state is released or removed.

Figure 6:
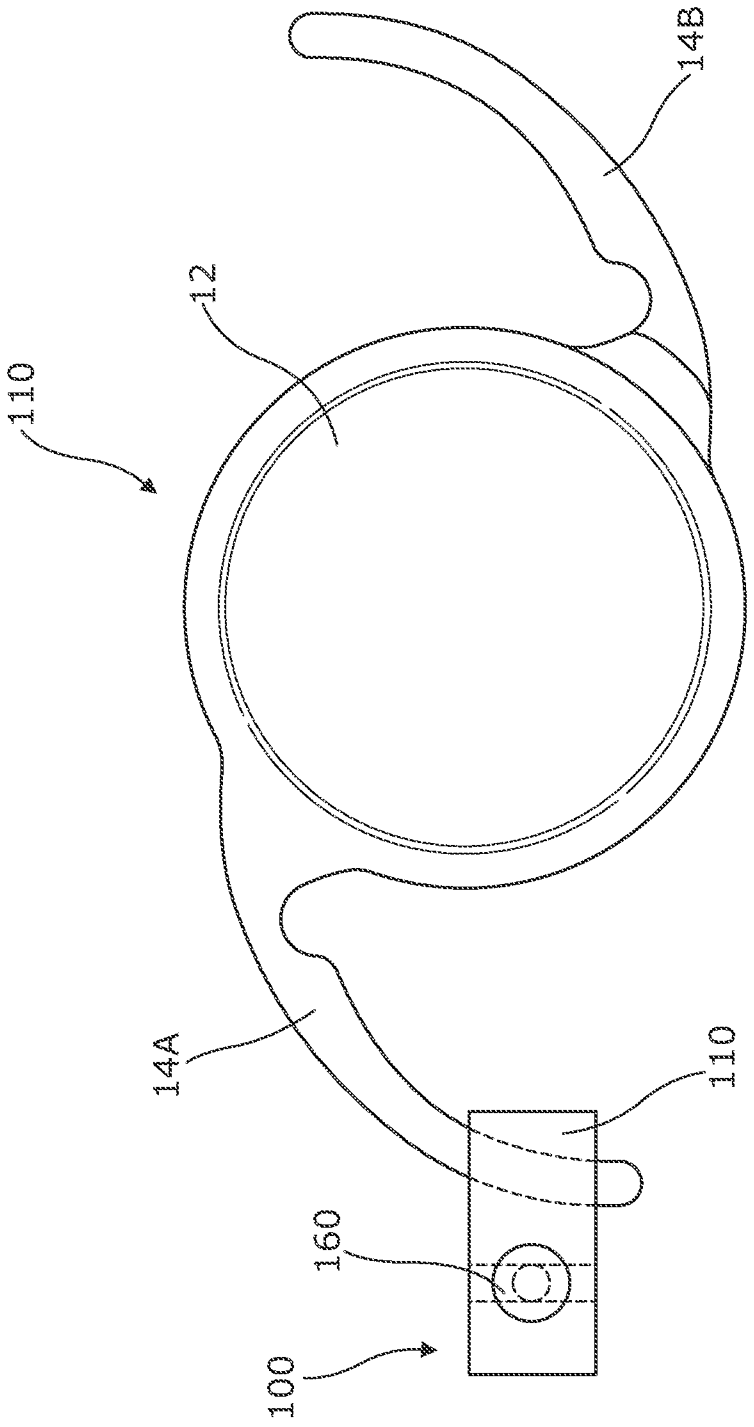
FIG. 6 shows an example of an IOL attached to an IOL clip according to an example of the present disclosure.

FIG. 6 is a plan view, showing how a first haptic 14A of an IOL 10 may be held between the arms of an IOL clip 100. As FIG. 6 is a top down view, it shows the first arm 110 of the IOL clip and the flange portion 160 of the IOL fixator, with dotted lines to indicate the position of the part of the IOL haptic 14A held beneath the first arm of the IOL clip. In practice, each haptic may be held by a separate IOL clip. So while FIG. 6 only shows one IOL clip 100 holding a first IOL haptic 14A, a second IOL clip may be used to hold the second haptic 14B. Further IOL clips may be used for IOLs with more than two haptics.

The hinge portion 130 of the IOL clip may be implemented in various ways. In some examples, the hinge portion 130 may comprise a single piece which joins the first arm and the second arm. The single piece hinge may loop around itself to define the aperture 180. In other examples, the hinge portion may comprise a plurality of parts, for instance interlocking parts, such as in a door hinge, which allow opening and closing of the clip by movement of one or both arms.

In some examples the hinge portion, first arm and second arm may formed as a single integral piece. This may be easier to manufacture and less prone to breaking than a hinge portion which is separate, but attached to, the first arm and the second arm. In other examples, the hinge portion may be made of a separate piece than the first and second arms. The hinge portion may be made of a material different from a material of the first arm and second arm. Having a hinge portion of a different material may increase the tensile strength of the hinge portion and may help the IOL to have a stronger bias or recoil to the closed state and thus a stronger gripping force.

Figure 7A:
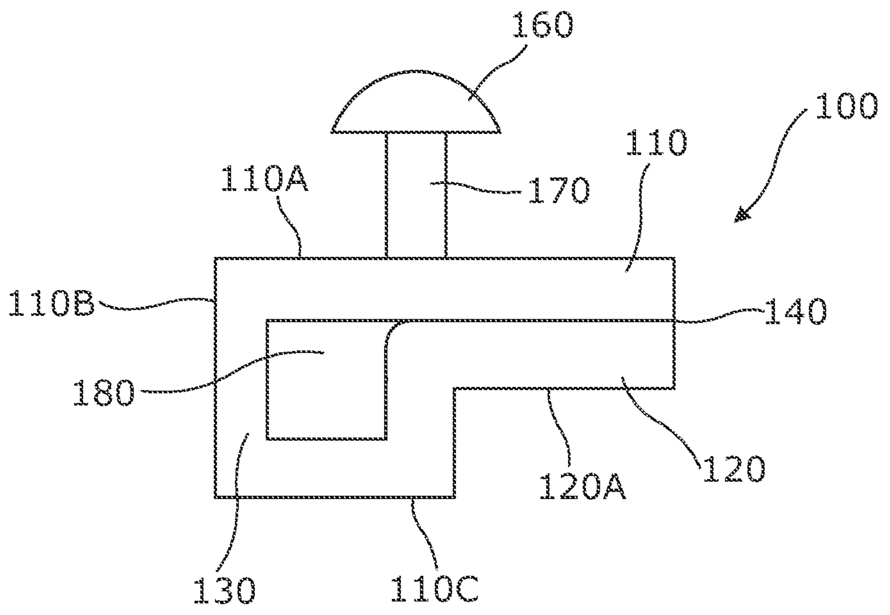
FIGS. 7A to 7B show another example of an IOL clip according to the present disclosure.
Figure 7B:
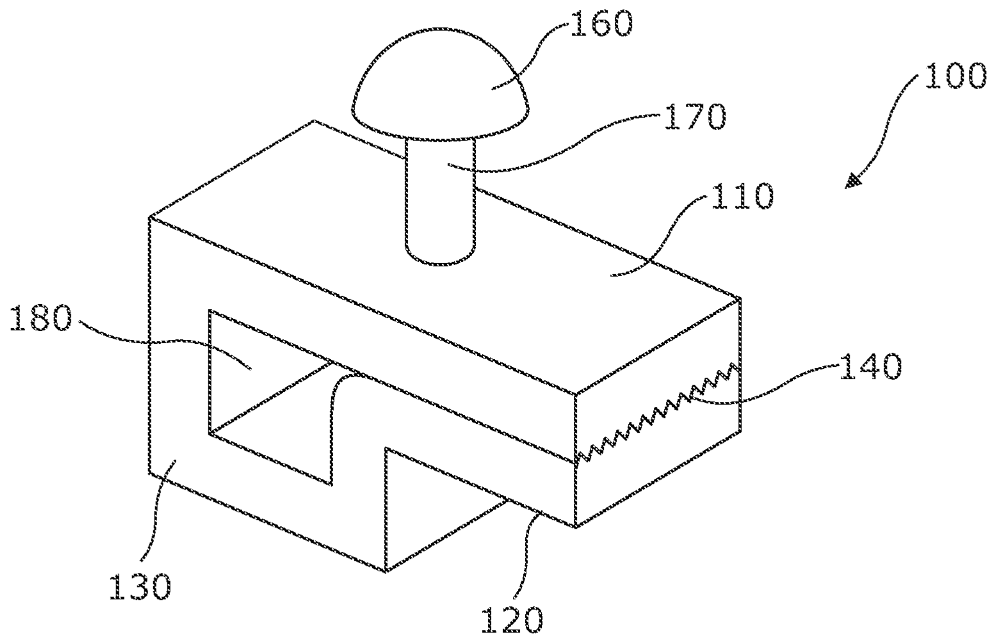

The hinge or joining portion 130 may be curved as this facilitates the opening and closing action and a smooth curve is less likely to cause damage to the eye. In some examples, the hinge portion 130 may be substantially ring shaped as shown in FIGS. 2A-2D, 3 and 4. In other examples, the hinge portion may include one or more straight portions or corners. In some examples the hinge portion may not be curved. For instance, the hinge portion may have a triangular shape, or may have a rectangular shape, or a square shape as shown in FIGS. 7A and 7B. In FIGS. 7A and 7B like reference numerals denote like parts as in FIGS. 2A to 2B.

The hinge or joining portion 130 may span an angle of between 270 degrees and 360 degrees between the first arm and the second arm when the IOL clip is in the closed state. For instance, where the hinge or joining portion 130 is a curved, the joining portion may define a curve of between 270 and 360 degrees. FIGS. 2A and 2B show a curve of approximately 360 degrees, but the joining portion may cover less than 360 degrees depending on the angle at which the joining portion joins the first arm and/or the second arm.

The IOL clip 100 may be formed of any material suitable for implantation into an eye, including but not limited to a plastic or polymer material, such as silicone or acrylic. The IOL clip may be biased to the closed state. In this way the clip will move back to the closed position once the opening force has been released. Biasing to the closed position makes the IOL clip convenient for use in surgery, as it allows automatic closure of the IOL clip to fasten to the IOL. The surgeon simply needs to release the opening force (e.g. stop pressing the spreading forceps handles together) to cause the arms of the clip to close around the IOL haptic.

In some examples, the IOL clip may have a length of between 3-6 mm. In some examples, the IOL clip may have a length of approximately 4 mm (e.g. 3.5 mm-4.5 mm). The length is in the longitudinal direction of the first and second arms, which may for example be the longest dimension of the clip and is in the direction left to right in FIGS. 2B and 7A. In some examples, the IOL clip may have a width of 1-3 mm. In some examples, the IOL clip may have a width of approximately 2 mm (e.g. 1.5 mm-2.5 mm). The width is in the direction left to right in FIG. 2C and is perpendicular to the length. The width may for example be measured across one of the arms. The width may be perpendicular to the length and substantially parallel to a line passing through an axis of the aperture 180. In some examples, the IOL clip may have a thickness of 1-3 mm. In some examples, the IOL clip may have a thickness of approximately 2 mm (e.g. 1.5 mm-2.5 mm). The thickness refers to the height of the clip and is in the direction top to bottom of FIG. 2C. The thickness may be measured in a direction passing through both the first arm and the second arm and perpendicular to the length. In some examples, the length of the shaft of the scleral fixator may be 0.4 mm to 0.8 mm. In some examples the length of the shaft may be from 0.5 to 0.7 mm and in other examples approximately 0.6 mm (e.g. 0.55 mm to 0.65 mm). The length of the shaft may be measured from the bottom of the flange to the face or surface of the arm or hinge portion which the shaft projects outwardly from.

In the examples of FIGS. 2A to 2D and 7A to 7B, the IOL clip 100 has a shape such that a center of the aperture 180 is beneath a plane of the first arm 110 and beneath a plane of the second arm 120, when the IOL clip is in the closed state. The IOL clip thus as a "q" shape. However, in other examples the center of the aperture 180 could be above the planes of the arms or between the planes of the arms in the closed position.

In the examples of FIGS. 2A to 2D and 7A to 7B, the scleral fixator 150 is positioned directly above a point where the hinge portion 130 meets the second arm 120. However, in other examples, the scleral fixator could have a different position. For instance, the scleral fixator may be positioned over the aperture, or at another position on the upper face of the first arm 110, on an outer face of the hinge portion 130, or an outer face of the second arm 120. The shaft 170 of the scleral fixator may extend from an outer face of the first arm, second arm or hinge portion (e.g. 110A, 110B, or 120A in FIG. 2A or FIG. 7A); as extending outwardly from a side of the arms or a side of the hinge would complicate the construction and may make the IOL clip more difficult to fasten to the sclera.

The IOL clip may have a shape such that the first arm 110 and the second arm 120 extend substantially parallel to each other when in the closed state. In some examples, for instance as shown in FIGS. 2A to 2D, the first arm and the second arm may be in contact with each other along their length when the IOL clip is in the closed position if no haptic is held there-between. The first arm 110 may be positioned above the second arm 120 and the hinge portion may have a shape (such as but not limited to a ring shape) which extends below the second arm.

Figure 8:
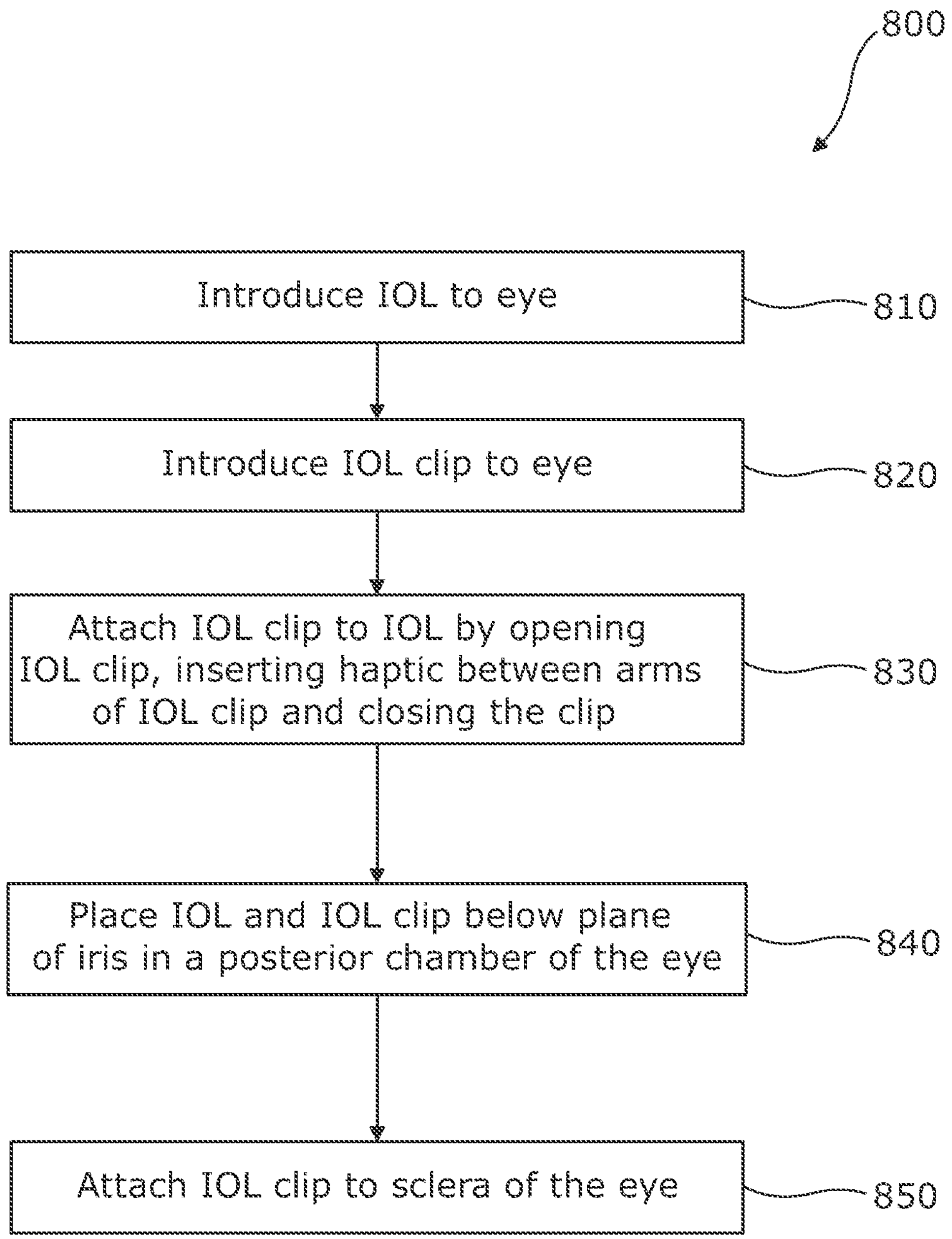
FIG. 8 shows an example method of fixing an IOL to the sclera of an eye using an IOL clip according to the present disclosure.
Figure 9:
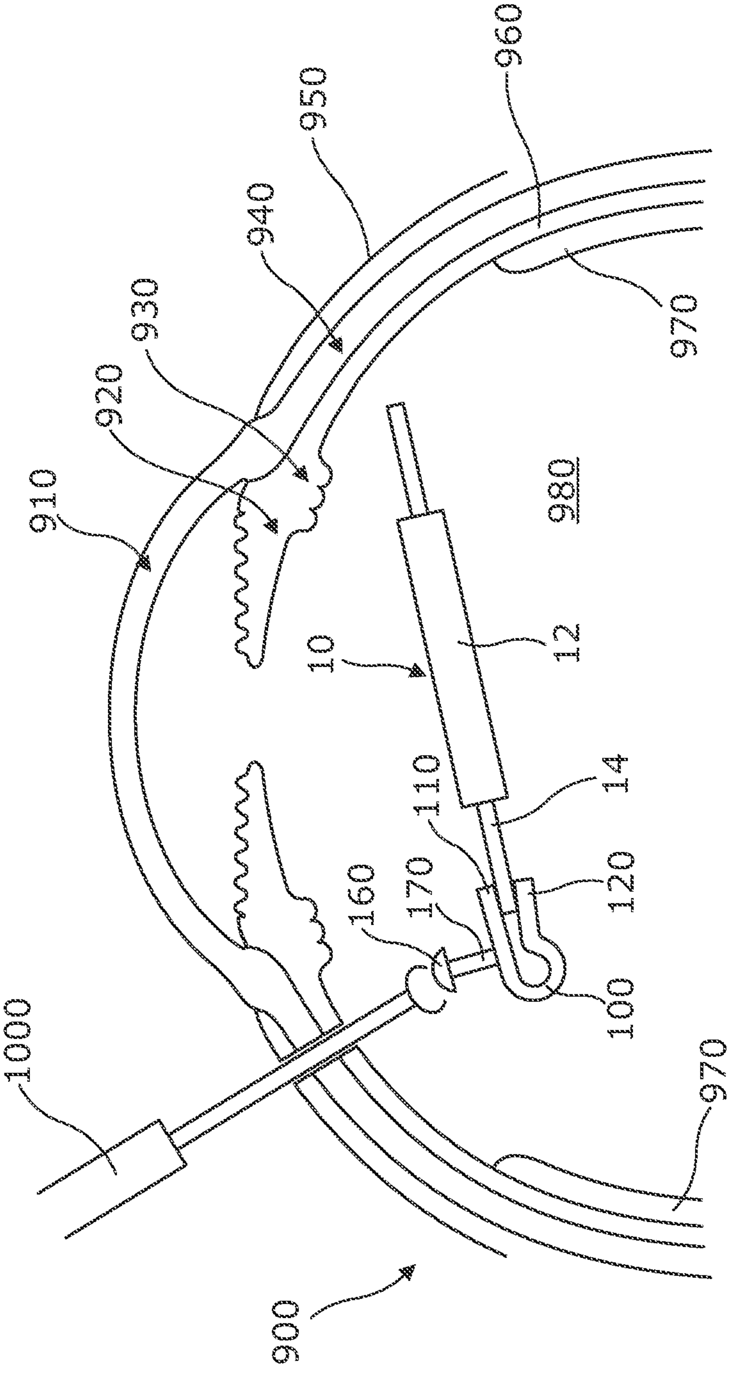
FIG. 9 shows an example of an IOL and an IOL clip according to the present disclosure being introduced into an eye.
Figure 10:
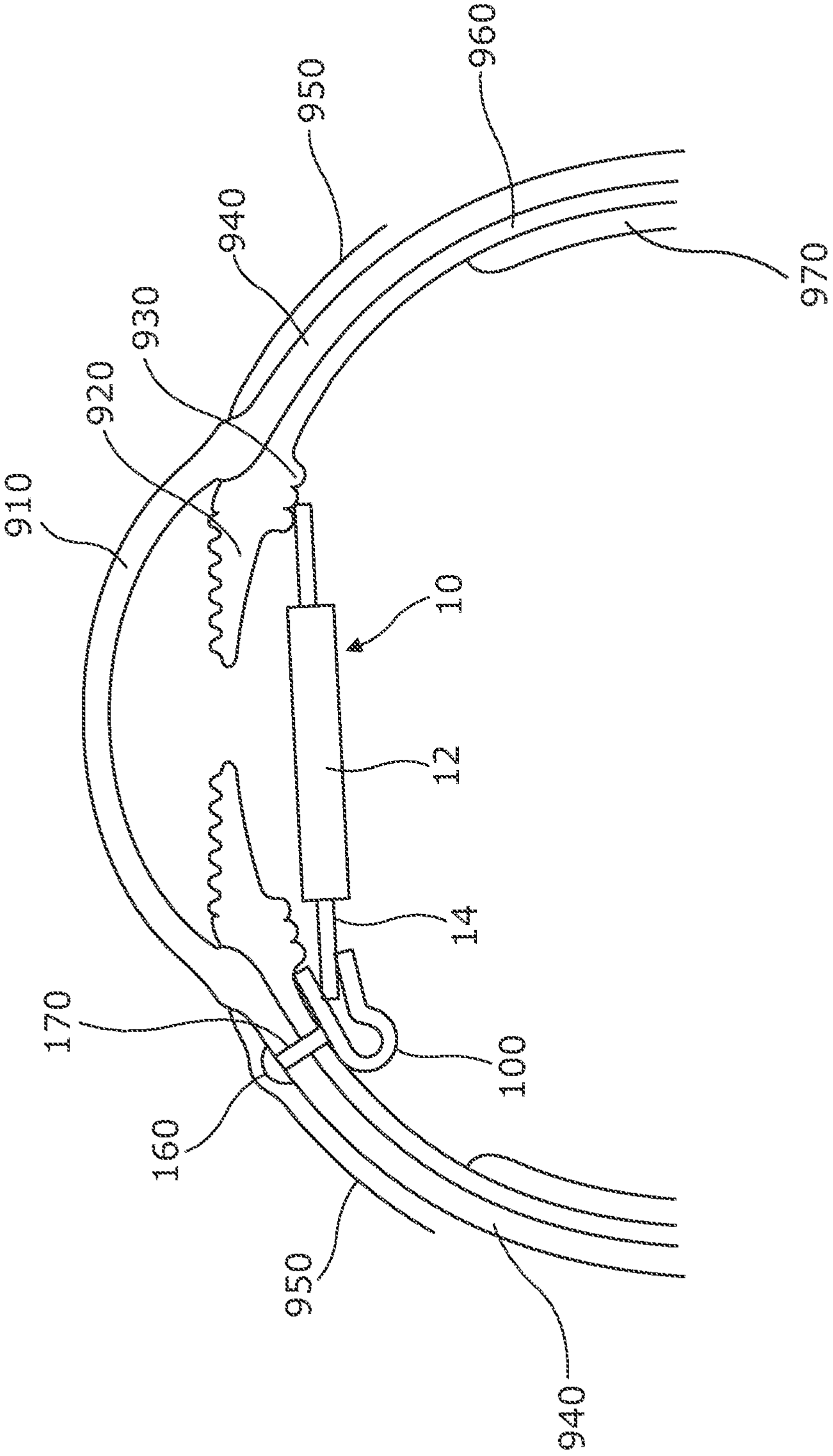
FIG. 10 shows an example of an IOL and an IOL clip according to the present disclosure which have been fixed to the sclera of an eye.

FIG. 8 is a flow diagram which shows one example of a method 800 of fixing an IOL to the sclera of an eye using an IOL clip according to the present disclosure. FIG. 9 shows an example of the IOL clip attached to the IOL inside the posterior chamber of the eye and prior to the IOL clip being attached to the sclera of the eye. FIG. 10 shows an example of the IOL clip and the IOL after the IOL clip has been attached to the sclera. The method 800 of FIG. 8 will now be described.

At block 810 the IOL is introduced into the eye.

At block 820 an IOL clip comprising a pair of opposing arms into the eye.

At block 830 the IOL clip is attached to the IOL by opening the IOL clip, inserting a haptic of the IOL between the arms of the clip and closing the clip to grip the haptic.

At block 840 the IOL and the IOL clip are placed below the plane of the iris in the posterior chamber of the eye.

At block 850 the IOL clip is attached to the sclera of the eye. For example, where the IOL clip has a scleral fixator comprising a shaft and a flange, the flange may be attached to the sclera.

While blocks 810 to 840 are shown sequentially in FIG. 8, these blocks may be carried in any order. For example, the IOL clip may be attached to the IOL prior to introducing the IOL clip and the IOL together into the eye.

FIG. 9 shows an eye comprising a cornea 910 which is the clear front window of the eye, an iris 920 which is the colored part of the eye, an anterior chamber between the cornea and the iris, and a posterior chamber 980 behind the iris. Also shown in FIG. 9 are the ciliary body 930 which is a structure containing muscle behind the iris, the sclera 940 which is a white outer coating of the eye surrounding the iris, the conjunctiva 950 which is a membrane that lines the inside of the eyelids and covers the sclera, the retina which is a nerve layer at the back of the eye which senses light, and the choroid 960 which is a layer containing blood vessels between the sclera and the retina.

The method 800 of FIG. 8 may be employed with an IOL clip as described in any of the examples herein. The IOL clip comprises a pair of opposing arms and may comprise a joining portion joining the arms. The IOL clip may comprises a scleral fixator extending from an outer surface of one of the opposing arms or from an outer surface of a joining portion joining the opposing arms. The scleral fixator may comprise a shaft for extending through the sclera of an eye and a flange for engaging with an anterior surface of the sclera of an eye.

In block 810 of method 800, the IOL is introduced into the eye. In some examples, the IOL may be introduced into the eye in block 810 by initially placing the IOL in a position at least partially above a plane of an iris of the eye. For example, the IOL may be placed with a first IOL haptic extending below the plane of the iris, or temporarily externalized through a scleral wound, and a second IOL haptic extending above the plane of the iris. This may facilitate better handling of the IOL, compared to initially placing both haptics below the iris plane, due to the limited space in the anterior chamber.

At block 820, the IOL clip is introduced into the eye. The IOL clip may be introduced into the eye by holding the IOL clip with a device. For example the IOL clip may be held by a pair of spreading forceps, such as but not limited to Watzke sleeve forceps, by inserting tips of the spreading forceps into the aperture of the joining portion of the IOL clip. In this way the IOL clip may be placed in the anterior chamber of the eye.

In block 830, the IOL clip is opened, this may for example be performed by using the device to open the IOL clip. For example, if the device is a pair of spreading forceps, opening the IOL clip may comprise moving tips of the spreading forceps apart to apply pressure to inner walls of the aperture so as to move the opposing arms of the IOL clip away from each other. For example, the surgeon's fingers holding the forceps may be pressed together so as to open the arms of the IOL clip.

At block 840, the IOL clip is attached to the IOL. In some examples, this may comprise aligning a plane of the IOL substantially parallel with a plane of the arms of the IOL clip, opening the arms and then closing the arms around the IOL haptic. In some examples, the method may comprise aligning a long axis of the IOL haptic substantially perpendicular to a long axis of the opposing arms of the IOL clip, as shown in FIG. 6. This may help to promote secure gripping of the IOL haptic by the arms of the IOL clip. In some examples, the method may comprise aligning the IOL clip so that the scleral fixator points up towards the cornea, before closing the arms of the IOL clip around the IOL haptic. Once the IOL clip has the correct alignment with the IOL, the arms of the IOL may be closed to firmly grip the haptic. For example, the force of the fingers pressing on the forceps may be lessened so as to close the arms of the IOL clip.

Once the IOL clip is engaged with the haptic of the IOL, the and the IOL clip may be placed below the iris plane, into the posterior chamber of the eye. The opening device, e.g. spreading forceps, is then withdrawn from the aperture 180 of the IOL clip and withdrawn from the anterior chamber.

At block 850 the IOL clip is attached to the sclera of the eye. For example, this may be done by forming a tunnel through the sclera and pulling a scleral fixator of the IOL clip through sclera so as to attach the IOL clip to the sclera. FIG. 9 shows a device 1000 for pulling the scleral fixator through the sclera. The device 1000 may, for example, be an end-gripping forceps.

Blocks 810-830 may be carried out in any order. For example, the IOL clip may be attached to the IOL before introducing the IOL into the eye, after introducing the IOL into the eye or while the IOL is partially inserted into the eye. In one example, the IOL clip is attached to the IOL when a leading haptic and the optic of the IOL are inside the eye and a trailing haptic is still outside the eye. In one example, the IOL may be folded before it is inserted into the eye and may unfold itself after introduction to the eye. In one example, a first haptic (referred to as the leading haptic) of the IOL may be inserted inside the eye together with the optic, while a second haptic (referred to as the trailing haptic) is still outside the eye when the IOL is unfolded. In that case, the IOL clip may be attached to the trailing haptic and then IOL clip and trailing haptic may be inserted together into the eye.

In some examples, a trocar and a microcannula insertor may be used to form the tunnel. For instance, an insertor such as, but not limited to, a 23-gauge vitrectomy set microcannula insertor may be used. In some examples, the microcannula may be removed and the trocar used to form the tunnel. The trocar may be used to form a full thickness transconjunctival tunnel in the sclera at a site proximate to, e.g. 2 mm away from, the limbus. Where two IOL clips are to be used, two full thickness tunnels may be made, one for each clip. In some examples, the tunnels may be approximately 180 degrees away from each other. In some examples, the tunnels are made at approximately at the 3 and 9 o'clock position of the eye.

An end gripping forceps may be used to pull the scleral fixator through the sclera. For example, a 23-gauge end gripping forceps may be used. The forceps may be inserted into the posterior chamber of the eye through the scleral tunnel made as described above. The tip of the end gripping forceps may be used to grasp the flange 160 and/or shaft 170 of the scleral fixator and pulls the IOL clip up until the flange 160 is externalized through the scleral tunnel, as shown in FIG. 10. The conjunctiva 950 may then be manipulated to cover the flange.

The same procedures may be repeated to attach one or more other IOL clips to any other haptics of the IOL, and externalise the flanges of the IOL clip scleral fixators through respective tunnels in the sclera. For example, where there are two haptics, the second haptic may be externalized through a second scleral tunnel at a 180 degrees to the first tunnel. In this way, multiple haptics of the IOL may securely fixated to the sclera of the eye so as to secure the IOL in place.

FIG. 10 shows the lens fixed to the sclera after the IOL clip has been attached to the sclera. In FIG. 10, the flange 160 the scleral fixator rests on an anterior surface of the sclera and the shaft 170 extends through the sclera. In this way the scleral fixator attaches the IOL clip to the sclera.

IOL clips according to some examples of the present disclosure may be used in a variety of situations. For example, the IOL clip may be used in a cataract operation where the capsule, the zonule, or both the capsule and zonule are damaged such that the IOL cannot be placed inside the capsule or cannot be placed in the sulcus between the iris and the capsular bag.

IOL clips according to some examples of the present disclosure may also be used where a patient has previously undergone a cataract operation and the existing IOL is subluxated or totally dislocated. In these cases the existing IOL can be removed and replaced with a new IOL. For example, the existing IOL may be removed using an IOL cutter and forceps to withdraw the existing IOL through a corneal wound; the residual capsular bag and zonule may be removed with anterior vitrectomy, and part of the anterior hyaloid may also be removed with anterior vitrectomy. A new IOL may then be injected and placed above the iris and the IOL clip may then be used as described above. On the other hand, if the existing subluxated or dislocated IOL is still of good quality, the existing IOL may be fixated using the IOL clip, and no new IOL is needed.

IOL clips according to some examples of the present disclosure may also be used in eyes which have not undergone a cataract operation before. For instance, eyes in which the crystalline lens is subluxated or dislocated (Ectopia Lentis) causing blurring of vision or other problems. In this case, the entire crystalline lens may be removed by phacofragmentation via a pars plana wound, and part of the anterior hyaloid may also be removed with anterior vitrectomy. A new IOL may then be inserted and placed above the iris and the IOL clip used as described above.

IOL clips according to some examples of the present disclosure may be used to fixate a partially malpositioned IOL. For example, the IOL clip could be used to fixate a slightly subluxated IOL when the capsular bag has a loose zonule at on side only. In such cases, the IOL clip may be used to stabilize one haptic of the IOL in order to re-centre the IOL.

The IOL clip of the present disclosure may be used to fix any type of IOL to the sclera of an eye and does not require any special design for the IOL. The IOL clip and associated method of fixation is thus very flexible and may be applied to one-piece IOLs, three-piece IOLs, IOLs with a variety of different shapes of haptic, IOLs with any number of haptics, rigid IOLs and foldable IOLs. The IOL does not need to be specially designed for scleral fixation and conventional IOLs for capsular implantation can be used. This flexibility is very useful, as it allows the surgeon to use any IOL in stock when performing surgery on patient.

For example, if an IOL is dropped or damaged during the procedure and the surgeon is using a suturing technique to fix the IOL, then the IOL must be replaced with a rigid IOL. If a rigid IOL having the preferred refractive power and colour is not available in the operating theatre at that time the operation might have to be postponed and the patient may have to become aphakic for a while. Likewise if the surgeon is using the Yamane technique to fix the IOL, then if the IOL is dropped or damaged, it must be replaced by a three-piece IOL having tubular haptics while a one-piece IOL cannot be substituted. However, by using a IOL clip according to the present disclosure, it is possible for the surgeon to fix any type of IOL to the desired location in the eye and the surgeon is not limited to a specific type of IOL.

Another consideration is that most multifocal IOLs are one-piece IOLs. Many fixation techniques do not work with one-piece IOLs. However, the method and IOL clip according to the present disclosure may be used with one-piece IOLs and thus make many multifocal IOLs available to patients with insufficient capsular support.

By providing the flexibility to work with a greater variety of IOLs, the present disclosure may also help to solve the issue of non-matching IOLs which do not match their fellow eye. For example, if restricted to a certain type of IOL (e.g. three-piece with tubular haptics), then due to lack of immediately available stock, a surgeon may have to use yellow IOL for one eye and a transparent IOL for the other eye, or to pair a monofocal IOL with a multifocal IOL/Extended depth of Focus (EDOF) IOL, or non-spheric IOL with a spheric IOL.

In some implementations, the method of implanting an IOL according to the present disclosure may be relatively simple to perform and may carry less risk of complications compared to suturing or the Yamane technique.

In some examples the flange of the scleral fixator may be a smooth dome shaped cap. This avoids erosion of the covering conjunctiva, which can happen with the Yamane technique or with unturned suture knots if suturing is used. Further, compared to some other fixation techniques, such as suturing, the IOL clip of the present disclosure may be less likely to accidentally break and may be easier to remove.

The IOL clip and methods described above may be used in a cataract surgery which encounters complications such as unplanned capsular rupture. Thus if the original surgery was planned with a particular IOL intended for capsular implantation, in the case of capsular rupture there is no need to switch to a specific IOL. Rather, the originally planned IOL can still be used and attached with the IOL clip according to the present disclosure. Whereas previously, if a surgeon was using a fixation technique limited to specific types of IOL and decided to switch a IOL during operation, if the operation theatre had no stock of the specific IOL meeting both the requirements of the fixation technique and optical requirements of the patient, the surgeon might have to postpone the surgery to implant the IOL. In that case the patient would have to be aphakic for a period of time while waiting for the next operation.

All of the features of the various example apparatus disclosed in this specification (including any accompanying claims, abstract and drawings), and/or all of the blocks of any method or process so disclosed, may be combined in any combination, except combinations where at least some of such features and/or blocks are mutually exclusive.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An intraocular lens (IOL) clip for fixing an IOL to the sclera of an eye, the IOL clip comprising:

a first arm;

a second arm opposing the first arm;

a hinge portion joining the first arm with the second arm and allowing movement of the IOL clip between an open state in which an IOL haptic can be introduced into a gap between the first arm and the second arm and a closed state for gripping the IOL haptic between the first arm and the second arm; and a scleral fixator for attaching the IOL clip to the sclera, the scleral fixator comprising a shaft extending outwardly from the first arm, the second arm or the hinge portion and a flange on the shaft for engaging the sclera, wherein the flange is a cap at the top of the shaft of the scleral fixator, and the cap has a smooth curved upper surface.

2. The IOL clip of claim 1 wherein the hinge portion has inner walls which define an aperture for receiving a device for opening the IOL clip; and the IOL clip is movable from the closed state to the open state by application of pressure to inner walls of the hinge portion.

3. The IOL clip of claim 1 wherein the hinge portion comprises a single piece which joins the first arm and the second arm and wherein the single piece loops around itself to define the aperture.

4. The IOL clip of claim 1 wherein the hinge portion is substantially ring-shaped.

5. The IOL clip of claim 1 wherein the first arm, second arm and hinge portion are formed as one integral piece.

6. The IOL clip of claim 1 wherein the IOL clip is biased to the closed state.

7. The IOL clip of claim 1 wherein an inner surface of the first arm and an inner surface of the second arm are textured to grip the IOL haptic.

8. The IOL clip of claim 7 wherein the inner surface of the first arm and the inner surface of the second arm are serrated.

9. The IOL clip of claim 1 wherein the IOL clip has a length of between 3 mm and 6 mm and wherein the shaft of the scleral fixator has a length of between 0.4 mm and 0.8 mm.

* * * * *